United States Patent [19]

Labaw et al.

[11] 4,374,996

[45] Feb. 22, 1983

[54] DISULFIDE INTERMEDIATE FOR CIMETIDINE

[75] Inventors: Clifford S. Labaw, Philadelphia; George R. Wellman, Wayne, both of Pa.

[73] Assignee: SK & F Lab Co., Carolina, P.R.

[21] Appl. No.: 270,076

[22] Filed: Jun. 3, 1981

[51] Int. Cl.$^3$ ............................................. C07D 233/64
[52] U.S. Cl. .................................................... 548/342
[58] Field of Search .......................................... 548/342

[56] References Cited

U.S. PATENT DOCUMENTS 3,950,333  4/1976  Durant et al. ................... 260/250 A
4,013,678  3/1977  Brown et al. ....................... 260/309

OTHER PUBLICATIONS

DeMarinis et al., *J. Org. Chem.*, vol. 42, pp. 2024–2025 (1977).
Harpp et al., *J. Am. Chem. Soc.*, vol. 93, pp. 2437–2445 (1971).

*Primary Examiner*—Henry R. Jiles
*Assistant Examiner*—N. Harkaway
*Attorney, Agent, or Firm*—Joan S. Keps; Richard D. Foggio; Alan D. Lourie

[57] ABSTRACT

A process for preparing cimetidine by sulfur extrusion from N-cyano-N'-methyl-N''-[2-(5-methyl-4-imidazolylmethyldithio)ethyl]guanidine.

1 Claim, No Drawings

DISULFIDE INTERMEDIATE FOR CIMETIDINE

This invention relates to a process for preparing cimetidine by sulfur extrusion from N-cyano-N'-methyl-N''-[2-(5-methyl-4-imidazolylmethyldithio)ethyl]-guanidine and to this new disulfide intermediate.

Cimetidine, N-cyano-N'-methyl-N''-[2-(5-methyl-4-imidazolylmethylthio)ethyl]guanidine, is a histamine $H_2$-receptor blocking agent of value as an inhibitor of gastric acid secretion. Cimetidine is widely used in the treatment of duodenal ulcers.

Methods of preparing cimetidine have been described. According to the process in U.S. Pat. No. 4,013,678, cimetidine is prepared by reacting 4-chloromethyl-5-methylimidazole hydrochloride with N-cyano-N'-methyl-N''-(2-mercaptoethyl)guanidine in the presence of a base. In U.S. Pat. No. 3,950,333, a procedure is described for reacting 4-hydroxymethyl-5-methylimidazole hydrochloride with cysteamine hydrochloride in acid to give 4-[(2-aminoethyl)thiomethyl]-5-methylimidazole dihydrochloride which is used as an intermediate to prepare cimetidine (by reaction with N-cyano-N',S-dimethylisothiourea).

According to the process of the present invention, cimetidine is prepared by the following procedure:

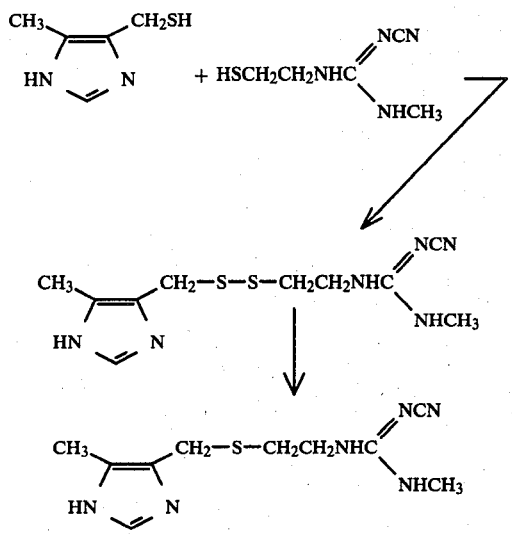

A mixture of 4-mercaptomethyl-5-methylimidazole and N-cyano-N'-methyl-N''-(2-mercaptoethyl)guanidine in solution is oxidized to give the disulfide compound. Preferably, approximately equimilar amounts of the two reagents are used. The reaction can be carried out in basic solution, for example in sodium hydroxide or potassium hydroxide in a solvent in which the reactants are soluble such as an aqueous lower alkanol, for example aqueous ethanol. An oxidizing agent such as a halogen for example chlorine or preferably iodine is added in a solvent such as ethanol to the mixture of the reagents in solution, preferably with cooling to about 0° C. Alternatively, the oxidation may be accomplished by blowing air or oxygen through the reaction mixture. The desired disulfide compound, N-cyano-N'-methyl-N''-[2-(5-methyl-4-imidazolylmethyldithio)ethyl]guanidine, is isolated from the reaction mixture for example by chromatography.

The N-cyano-N'-methyl-N''-[2-(5-methyl-4-imidazolylmethyldithio)ethyl]guanidine is reacted with a phosphine such as an aminophosphine, for example hexamethylphosphorus triamide. The sulfur extrusion process can be carried out in a polar non-reactive organic solvent in which the reactants are soluble, such as tetrahydrofuran, benzonitrile, ethyl acetate or, preferably, acetonitrile, at about room temperature.

The invention is illustrated by the following example. The temperatures indicated therein are in degrees Centigrade.

EXAMPLE 1

Aqueous sodium hydroxide (3.60 g, 0.9 mol) was added to a stirred ethanolic solution of 5-methyl-4-mercaptomethylimidazole hydrochloride (5.92 g, 0.03 mol) and N-cyano-N'-methyl-N''-(2-mercaptoethyl)guanidine (5.74 g, 0.0363 mol). The solution was cooled to 0° and a saturated ethanolic solution of iodine was added until the iodine color remained. The solvent was removed under reduced pressure to yield an oil which was purified using preparative high pressure liquid chromatography (silica gel; 13% methanol in ethyl acetate). The glassy product obtained was triturated with acetonitrile to yield N-cyano-N'-methyl-N''-[2-(5-methyl-4-imidazolylmethyldithio)ethyl]guanidine, m.p. 137°-142°; Ms m/e 284.

Hexamethylphosphorus triamide (1.87 g, 5.3 mmol) was added to N-cyano-N'-methyl-N''-[2-(5-methyl-4-imidazolylmethyldithio)ethyl]guanidine (240 mg, 0.84 mmol) suspended in acetonitrile. The reaction mixture was allowed to stand for 16 hours after which time all the materials had dissolved. Analytical high pressure liquid chromatography (silica gel; 1000:60:20:5—acetonitrile, methanol, water and ammonium hydroxide) gave a solution containing N-cyano-N'-methyl-N''-[2-(5-methyl-4-imidazolylmethylthio)ethyl]guanidine (yield about 56%). An analytical sample of the product obtained after removal of solvent was isolated by preparative high pressure liquid chromatography using similar conditions as above to yield an oil which on standing in 1 ml of isopropyl alcohol gave N-cyano-N'-methyl-N''-[2-(5-methyl-4-imidazolylmethylthio)ethyl]guanidine.

What is claimed is:

1. N-cyano-N'-methyl-N''-[2-(5-methyl-4-imidazolylmethyldithio)ethyl]guanidine.

* * * * *